(12) United States Patent
Brooks-Korn

(10) Patent No.: US 8,410,129 B2
(45) Date of Patent: Apr. 2, 2013

(54) TREATMENT FOR PARESIS/PARALYSIS

(76) Inventor: Howard Brooks-Korn, Millbrae, CA (US)

( * ) Notice: Subject to any disclaimer, the term of this patent is extended or adjusted under 35 U.S.C. 154(b) by 3059 days.

(21) Appl. No.: 10/367,386

(22) Filed: Feb. 14, 2003

(65) Prior Publication Data

US 2003/0166670 A1    Sep. 4, 2003

Related U.S. Application Data

(60) Provisional application No. 60/357,389, filed on Feb. 15, 2002.

(51) Int. Cl.
*A01N 43/42* (2006.01)
*A61K 31/44* (2006.01)

(52) U.S. Cl. ..................................................... 514/282

(58) Field of Classification Search .................. 514/175, 514/169, 282
See application file for complete search history.

(56) References Cited

U.S. PATENT DOCUMENTS

| | | | | |
|---|---|---|---|---|
| 4,803,208 | A | 2/1989 | Pasternak | 514/282 |
| 4,816,586 | A | 3/1989 | Portoghese | 544/340 |
| 5,317,022 | A * | 5/1994 | Borsodi et al. | 514/282 |
| 5,352,680 | A | 10/1994 | Portoghese et al. | 514/279 |
| 5,393,545 | A * | 2/1995 | Johnson et al. | 426/268 |
| 5,958,459 | A | 9/1999 | Chasin et al. | 424/490 |
| 6,103,261 | A | 8/2000 | Chasin et al. | 424/459 |
| 6,136,817 | A | 10/2000 | Schmidhammer | 514/279 |
| 6,150,524 | A | 11/2000 | Hartmann et al. | 546/44 |
| 6,162,467 | A | 12/2000 | Miller et al. | 424/468 |
| 6,294,195 | B1 | 9/2001 | Oshlack et al. | 424/457 |
| 6,365,742 | B1 | 4/2002 | Mudryk et al. | 546/44 |
| 6,476,044 | B1 | 11/2002 | Wnendt et al. | 514/282 |
| 6,706,704 | B2 * | 3/2004 | Lalley | 514/217.02 |

FOREIGN PATENT DOCUMENTS

| | | | |
|---|---|---|---|
| WO | WO 01/05795 | A1 | 1/2001 |
| WO | WO 01/12195 | A2 | 2/2001 |

OTHER PUBLICATIONS

Longer et al. (Remington's Pharmaceutical Sciences 18th Edition, Chapter 91, 1990, p. 1676-1682).*
Kahn, S. & Smith, M, "beta-Endorphin and Muscle Contraction," Muscle & Nerve 18:1250-1256 (1995).
Kahn, S. & Smith, M, "Actions of Endorphin Peptides on Muscle," Peptides, vol. 8, No. 1, 87-92 (1997).
Kalman, S. et al., "Morphine and Multiple Sclerosis," European J. Pain, 6:69-80 (2002).
Braund, et al., (1994) "Clinical Syndromes in Veterinary Neurology" 2d Edition [Table of Contents Provided].
Gaynor, et al., (1997) "Risk Factors for Acquired Megaesophagus in Dogs" *J. Am. Vet. Med. Assoc.* 211(11):1406-12.
Isozaki, et al., (1996) "Early Diagnosis and Stage Classification of Vocal Cord Abductor Paralysis in Patients with Multiple System Atrophy" *J. Neurol. Neurosurg. Psychiatry* 60(4):399-402.
Ooi, (1992) "B-Mode Real-Time Ultrasound Assessment of Vocal Cord Function in Recurrent Laryngeal Nerve Palsy" *Ann. Acad. Med. Singapore* 21(2):214-216.
Osei-Lah, et al., (1999) "Bilateral Abductor Vocal Fold Paralysis Due to Myasthenia Gravis" *J. Laryngol. Otol.* 113(7):678-679.
Reisine, et al., (1996) "Opioid Analgesics and Antagonists" *The Pharmacological Basis of Therapeutics*, 9th Edition, pp. 521-555.
Remington's Pharmaceutical Sciences 443 (1975) [Table of Contents Provided].
Remington, (1995) "The Science and Practice of Pharmacy," vol. I, 19th Edition, [Table of Contents Provided].
Remington, (1995) "The Science and Practice of Pharmacy," vol. II, 19th Edition, [Table of Contents Provided].
Schurig, et al., (1982) Antiemetic Activity of Butorphanol Against Cisplatin-Induced Emesis in Ferrets and Dogs, *Cancer Treatment Rep.* 66(10):1831-1835.
International Search Report dated Aug. 8, 2003.

* cited by examiner

*Primary Examiner* — Yong Chong
(74) *Attorney, Agent, or Firm* — David A. Lowin

(57) ABSTRACT

The present invention relates to a novel use of opioid compounds for treatment of a neurologic or neurogenic disorder. Such neurologic or neurogenic disorders include lingual, pharyngeal, laryngeal, esophageal, urinary bladder sphincter, lumbar and lumbo-sacral spine, and pelvis and pelvic limb paresis/paralysis. The invention provides a unique method of treating a specified disorder or syndrome by administering to a subject in need of such treatment a therapeutically effective amount of an opioid compound.

25 Claims, No Drawings

TREATMENT FOR PARESIS/PARALYSIS

This application claims priority to U.S. Provisional Application 60/357,389, filed Feb. 15, 2002.

TECHNICAL FIELD

This invention relates generally to methods and pharmaceutical compositions for treating neurologic and neurogenic disorders of the mammalian nervous system. Specifically, the invention relates to a novel use of opioid compounds for treatment of centrally and peripherally mediated neuropathies and neuromyopathies. The list of opioid-treatable neuropathies and neuromyopathies includes but is not limited to lingual, pharyngeal, laryngeal, esophageal, urinary bladder sphincter, lumbar and lumbo-sacral spine, pelvis and pelvic-limb paresis or paralysis.

BACKGROUND OF THE INVENTION

Overview of the Mammalian Nervous System

The mammalian nervous system is comprised of the Central and Peripheral Nervous Systems. The Central Nervous System ("CNS") is comprised of the brain and its functional components. The Peripheral Nervous System ("PNS") is comprised of all the cranial and spinal nerves and their functional components. Paired cranial and spinal nerves provide the means of communication between the brain, the spinal cord and the rest of the body.

In disorders of the nervous system, when the cause originates from outside the nervous system the disorder is termed "neurologic," and when the cause originates from within the nervous system it is termed "neurogenic." Such disorders can be identified as a part of a larger neurologic or neurogenic syndrome, where a "syndrome" is defined as two or more disorders and their clinical signs occurring together to form a recognized disease state. When the clinical signs associated with a disorder or a syndrome are the result of the dysfunction of a single nerve it is referred to as a "neuropathy," and when the clinical signs are the result of the dysfunction of two or more individual nerves, it is referred to as a "polyneuropathy." The dysfunctioning nerves in a polyneuropathy can be located in either the CNS, the PNS, or in both nervous systems simultaneously.

Disorders involving the CNS, the PNS, or both systems together will impact the area(s) of the body normally innervated by that system or systems. In the disorders treated with the methods and uses of the present invention, the area impacted by nervous system dysfunction is the muscle tissue, resulting in a partial or total loss of muscular function termed a "neuromyopathy." These disorders are observed individually or as part of a larger neurologic and/or neurogenic syndrome, and can be inherited or acquired. When partial function remains in the innervated muscle tissue, it is termed "paresis." When no function remains in the innervated muscle tissue, it is termed "paralysis."

Lingual paresis/paralysis affects the ability of an individual to prehend food, pass a food bolus to the back of the pharynx and interferes with the individual's ability to swallow food, saliva or water; the resulting disorder is known as "Oral or Lingual Dysphagia." If the individual's nutritional needs are not effectively addressed, death can occur as the result of the body's physical deterioration and eventual organ shutdown from the prolonged effects of dehydration, malnutrition and eventual starvation. To date there is no known cure for lingual paresis/paralysis. The focus of therapy remains on strategies to insure an adequate dietary intake of food and water and management of effective oral hygiene.

Pharyngeal paresis/paralysis can disrupt the normal gag and or swallow reflexes resulting in the ineffective swallowing of food and water, can lead to aspiration pneumonia as the opening into the trachea is ineffectively covered during swallowing, can allow regurgitation of food or fluid back up into the oral and nasal cavities and can impair the normal passage of air into the trachea; the resulting disorder is known as "Pharyngeal Dysphagia." If an individual's nutritional and airway needs are not adequately addressed, death can occur as the result of complications of starvation and or aspiration pneumonia. To date there is no known cure for pharyngeal paresis/paralysis. The focus of therapy remains on strategies to insure adequate nutritional intake while addressing continual problems associated with fluid and food aspiration into the lungs.

Laryngeal paresis/paralysis can impair one's ability to phonate, can cause an upper airway obstructive syndrome severely decreasing airflow into the lungs, and can allow aspiration of food and fluid into the trachea as the arytenoids fail to effectively close over its opening; the resulting disorder is known as "Laryngeal Dysphagia." If the medical affects of laryngeal paresis/paralysis are not effectively dealt with, death may occur as the result of complications from aspiration pneumonia, respiratory failure and finally cardiac arrest. To date there is no known cure for laryngeal paresis/paralysis. The focus of therapy remains on strategies to maintain an open and adequate airway into the trachea allowing sufficient oxygen to reach the lungs and on strategies to deal with aspiration pneumonia and its consequences.

Esophageal paresis/paralysis can result in retention of masticated food and fluid in the esophagus and can lead to retention esophagitis, which can result in regurgitation of esophageal contents into the oral and nasal pharynx, and can allow aspiration of the regurgitated esophageal contents into the lungs; the resulting disorder is known as "Megaesophagus." Death from "Megaesophagus" may ensue from the long-term effects of starvation, as a result of complications of "Retention Esophagitis", and/or from the secondary complications of aspiration pneumonia. To date there is no known cure for esophageal paresis/paralysis. The focus of therapy remains on strategies to passively allow masticated food and fluid to flow from the oral pharynx to the stomach, and on medical strategies for treating the resultant esophagitis including neutralizing the affects of differing chemical compositions on mucosal surfaces when positional aids fail to prevent movement of foodstuffs passively back out into the oral/nasal pharynx.

Urinary bladder sphincter paresis/paralysis can result in intermittent or continual leaking of urine out of the bladder; the resulting disorder is known as "Neurogenic Urinary Bladder Sphincter Incontinence." The leaking urine's pathway or site of accumulation determines the symptoms associated with this incontinence. Urethritis, Cystitis, Nephritis, Vaginitis, Perivulvar and Vulvar Vaginitis and Urine Scald Dermatitis are some of the secondary consequences associated with urinary bladder sphincter paresis/paralysis. To date there is no known cure for urinary bladder sphincter paresis/paralysis. The focus of therapy remains on strategies to control urine leakage (as in Urinary Bladder Suspension Surgery), or to absorb the leaking urine (using absorbent sanitary pads or undergarments), to treat primary and secondary areas of inflammation or infection, and to keep the leaking and leaked on areas as clean, dry, and sanitary as possible.

Lumbar and lumbo-sacral spine paresis/paralysis can cause progressive atrophy and weakness of the skeletal muscles over the lumbar and sacral spine. As the disorder progresses, it becomes increasingly more difficult to use the back in even the most basic of functions such as in bending, straightening and turning the upper torso. To date there is no known cure for lumbar and lumbo-sacral spine paresis/paralysis. The focus of therapy remains on strategies to assist one with ambulation, sitting, standing and reclining such as specially designed walkers, canes, rails, ramps, power assisted lifts, etc.

Pelvis and pelvic limb paresis/paralysis causes progressive atrophy, weakness and eventual paralysis of the muscles which make up the pelvis and pelvic limbs. Progressive loss of muscle tone and strength in the pelvis and pelvic limbs make even rudimentary functions such as standing, sitting, rising, and ambulating almost impossible without some sort of external assistance. To date there is no known cure for pelvis and pelvic limb paresis/paralysis. The focus of therapy remains on strategies for assisted movements when standing, walking or sitting, such as specially designed walkers, canes, crutches and carts. Eventually any function requiring muscular movement or strength below the waist will fail.

These disorders or syndromes of neurologic or neurogenic origin are often progressive in nature and can eventually result in permanent dysfunction of the particular organ or area of the body involved. As only palliative treatment is currently available to those suffering from such debilitating conditions, there exists a considerable need for better therapeutic choices and ultimately a cure for these disorders, as well as disease states seen individually or as part of a larger neurologic or neurogenic disorder or syndrome, and polyneuropathic syndromes that contain some or all of these neurologic or neurogenic signs and symptoms.

The Opioids: Mechanism of Action

Opioids are alkaloid compounds. The prototypic opioid, morphine, was first isolated from opium in the early nineteenth century. The opium alkaloids can be broadly divided into five distinct chemical classes: phenanthrene, benzylisoquinoline, tetrahydroisoquinoline, cryptopine, and miscellaneous (Remington's Pharmaceutical Sciences 433, 1975). Therapeutically useful drugs are primarily isolated from the phenanthrene and benzylisoquinoline classes. The principal phenanthrenes are morphine, codeine, and thebaine. The principal benzylisoquinolines are papaverine and noscapine.

The most common use of opioid compounds in today's prescription market is for their analgesic properties. The opioids produce their effects by binding to different types of opioid receptors throughout the central and peripheral nervous systems. Opioids act within the central nervous system to elevate the pain threshold and to alter the psychological response to pain. The opioids act outside the brain, producing their pharmacologic effects by interacting with one or more of four (three major) opioid receptors (mu, sigma, kappa, and delta) located in the peripheral nervous system. The pharmacologic effects vary among opioid derivatives, depending on the receptor, its location in the body, and the type of interaction between the opioid derivative and the receptor. It is currently understood that a given opioid derivative can bind with one or more types of opioid receptors, and believed likely that several subtypes of receptors exist for each of the three major types of receptors (mu, delta, and kappa).

Although the primary pharmacologic effects desired from most all opioids in use today are analgesia, euphoria, and sedation without loss of consciousness (Reisine and Pasternak, 1966), the pharmacologic effects of opioids are now known to extend beyond the control of pain. One opioid derivative, apomorphine, directly stimulates the chemoreceptor trigger zone in the brain, triggering an emetic or vomiting response, which can be helpful in an emergency situation where one wants to stimulate a vomiting response. Butorphanol, another opioid derivative, has been used as an antiemetic, to help control the vomiting induced by the chemotherapeutic agent Cisplatin (Schurig, et al., 1982). Additional gastrointestinal effects noted in response to the administration of opioid compounds include, increase or decrease in the amount of hydrochloric acid secreted into the stomach, increase in tone in the antral portion of the stomach and upper duodenum, resting segmental tone is increased, markedly decreasing the propulsive movement of the intestinal contents, which is helpful in treating upper intestinal diarrhea, but can lead to the common problem of constipation if diarrhea is not present.

SUMMARY OF THE INVENTION

The present invention for the first time, establishes the in vivo therapeutic (non-analgesic) utility of the opioid class of compounds not for the treatment of pain, but for the treatment of a number of specified neurologic or neurogenic disorders. Naturally occurring, endogenous opioid peptides (opiopeptins) have been shown to act as neurotransmitters and appear to act as modulators of neurotransmission or as neurohormones, as have several opium derivatives found in nature (morphine, codeine and other related compounds) (Reisine and Pasternak). It is in this role, i.e., endogenous opioid peptide neurotransmitter replacement or neurohormone, that the opioids are believed to exert their effect on the paretic or paralyzed muscle tissue, partially or completely reversing the paresis/paralysis.

The present invention encompasses the novel use of an opioid compound to treat a neurologic or neurogenic disorder. Such disorder can be selected from the group: lingual paresis/paralysis, pharyngeal paresis/paralysis, laryngeal paresis/paralysis, esophageal paresis/paralysis, urinary bladder sphincter paresis/paralysis, lumbar and lumbo-sacral spine paresis/paralysis, and pelvis and pelvic limb paresis/paralysis. In another aspect, the invention encompasses the novel use of an opioid compound to treat a syndrome including more than one of the above-mentioned disorders.

Another aspect of the present invention is the novel use of an opioid compound to individually treat disease states or symptoms identified previously as part of a disorder or syndrome including, but not limited to: Cardiomyopathy, Centrally Mediated Depression, Congestive Heart Failure and Paralytic Intestinal Ileus.

Another aspect of the present invention is the novel use of opioid compounds to treat paresis/paralysis in one or more polyneuropathic syndromes characterized by similar neurologic or neurogenic signs and symptoms, including, but not limited to: Multiple Autonomic Nervous System Dysfunction, Multiple Sclerosis, Muscular Dystrophy, Myasthenia Gravis and Parkinson's Disease.

The present invention further encompasses a method for treating a neurologic or neurogenic disorder comprising administering to a subject in need of such treatment a therapeutically effective amount of a pharmaceutical formulation comprising an opioid compound. Such pharmaceutical formulations can be immediate or sustained release.

The opioid compound useful in practice of the invention include naturally occurring opium alkaloids, semi-synthetic opium alkaloids and synthetic opium alkaloids. One preferred group of naturally occurring opium alkaloid includes: morphine, codeine, thebaine, papaverine, and noscapine, or a pharmaceutically or veterinarily acceptable salt thereof. A preferred group of semi-synthetic opium alkaloids includes: heroin, hydromorphone, metapon, oxymorphone, levorphanol, hydrocodone, oxycodone, tramadol, nalorphine, naloxone, or naltrexone, or a pharmaceutically or veterinarily acceptable salt thereof. A preferred group of synthetic opium alkaloids includes: meperidine and congners, methadone and congeners, levorphanol and congeners, phenazocine, fentanyl, propoxyphene and ethoheptazine, or a pharmaceutically or veterinarily acceptable salt thereof. Also preferred, individually and collectively, are the opioid compounds/formulations employed in the Examples: oxycodone, morphine, oxycodone hydrochloride immediate or sustained release, and morphine sulphate immediate or sustained release, especially oxycodone hydrochloride sustained release.

Administration of the pharmaceutical formulation is carried out within the context of a predetermined dosing regimen such that the agent is effective in the treatment of the specified neurologic/neurogenic disorder. The precise amount of the pharmaceutically effective medication administered will generally depend on the particular drug selected, the age and general condition, and, or, the pharmacological condition of the subject being treated, and the judgment of the prescribing physician. In general the subject is given a daily dose of the effective opioid in the range of approximately 0.1 mg to 200 mg depending on the amount needed to sustain a therapeutic blood level, administered preferably, but not limited to, one to eight times in a twenty-four hour period. The drug delivery may be by, but not limited to, oral, intravenous, intramuscular, subcutaneous, transdermal or another acceptable route.

DETAILED DESCRIPTION OF THE INVENTION

Throughout this disclosure, various publications, patents and published patent specifications are referenced by an identifying citation. The disclosures of these publications, patents and published patent specifications are hereby incorporated by reference into the present disclosure.

DEFINITIONS

As used in the specifications and claims, the singular form "a", "an" and "the" include plural references unless the context clearly dictates otherwise. For example, the term "an opioid compound" includes a plurality of opioids, including mixtures thereof.

Before describing the present invention in detail, it is to be understood that this invention is not limited to particular drugs or drug delivery systems, and as such may vary. It is also to be understood that the terminology used herein is for the purpose of describing particular embodiments only, and is not intended to be limiting.

The terms "treat", "treating" and "treatment" as used herein, includes preventing, ameliorating, reducing or curing a disease state, disorder or syndrome; effecting a reduction in severity and/or frequency of symptoms, elimination of symptoms and/or underlying cause, prevention of the occurrence of symptoms or their underlying cause, and/or amelioration of damage caused thereby, e.g., partially or completely reversing paresis/paralysis. The present method of "treating" a neurologic/neurogenic disorder, as the term is used herein, thus encompasses both predisposed individuals and clinically symptomatic individuals.

The terms "active agent," "drug" and "pharmacologically active agent" are used interchangeably herein to refer to a chemical material or compound that induces a desired effect. In the preferred embodiment herein, the terms refer to an opioid compound. Included are derivatives and analogs of those compounds or classes of compounds specifically mentioned herein or known in the art, which also induce the desired effect.

The terms "opioid compound" and "opioids" refer to substances (natural, semisynthetic or synthetic) that bind to a centrally and/or peripherally located opioid receptor to produce an agonist action, a partial agonistic action (agonist/antagonist) or an antagonist action, including the opioid compounds described below.

"Carriers" or "vehicles" as used herein refer to carrier materials suitable for drug administration. Carriers and vehicles useful herein include, but are not limited to any such material known in the art, which is nontoxic and does not interact with other components of the composition in a deleterious manner.

By a "therapeutically effective" is meant a nontoxic but sufficient amount of the drug, agent or formulation to provide the desired effect, i.e., treatment of a neurologic/neurogenic disorder that causes paresis/paralysis.

"Paresis/paralysis" is defined for purposes of the present invention as partial or total loss of function in innervated muscle tissue resulting from a neurologic or neurogenic disorder.

"Immediate-release" is defined for purposes of the present invention as the release of the drug (e.g., opioid compound) at such a rate that therapeutic blood (e.g., plasma) levels required by the body are reached, and maintained for a period 6 hours or less.

"Extended or sustained-release" is defined for purposes of the present invention as the release of the drug (e.g., opioid compound) at such a rate that therapeutic blood (e.g. plasma) levels required by the body are reached and maintained for a period lasting over 6 hours and preferably lasting 12-36 hours or longer.

The terms "subject," "individual" or "patient" are used interchangeably herein, referring to a vertebrate, preferably a mammal. The mammal is either a human or a non-human. Non-human mammals include but are not limited to, mice (murines), rats, simians, farm animals, sport animals, and pets such as dogs and cats.

Neurologic/Neurogenic Disorders and Syndromes Treated

The present invention provides a novel use for an existing class of compounds, the opioids, to effectively treat neurologic/neurogenic disorders and syndromes. One of the results of such treatment is the cessation and/or reversal of the atrophy or wasting of the affected muscle(s).

One such group of disorders includes (without limitation) lingual, pharyngeal, laryngeal, esophageal, urinary bladder sphincter, lumbar and lumbo-sacral spine, and pelvis and pelvic limb paresis/paralysis, whether identified alone or as part of a larger neurologic or neurogenic syndrome.

Examples of disease states seen individually or as part of a larger neurologic or neurogenic disorder or syndrome, which respond individually to treatment with one or more opioid compound(s) according to the present invention include, but are not limited to, Cardiomyopathy, Centrally Mediated Depression, Congestive Heart Failure, and Paralytic Intestinal Ileus.

Examples of polyneuropathic syndromes that contain some or all of the neurologic or neurogenic signs and symptoms, which respond individually to treatment with one or more opioid compound(s) according to the present invention include, but are not limited to, Multiple Autonomic Nervous System Dysfunction, Multiple Sclerosis, Muscular Dystrophy, Myasthenia Gravis and Parkinson's Disease.

Identification of the specific nerve or group of nerves associated with a neurologic or neurogenic disorder or polyneuropathic syndrome with their attendant clinical signs and symptoms, and documenting which of the opioid compound(s) used in the present invention effectively treats the associated disease signs and symptoms, provides a unique opportunity to apply this knowledge to the treatment of other disease states caused by a neuropathic disorder or polyneuropathic syndrome, which contain some or all of these same effectively treated clinical signs and symptoms as part of their signalment.

Active Agents Employed in the Methods of the Invention

In order to carry out the method of the invention, an opioid compound is administered to an individual prone to or exhibiting one or more neurologic or neurogenic disorders or symptoms of paresis/paralysis affecting a voluntary or involuntary muscle, or a group of muscles.

In one embodiment, the opioid compound is capable of binding to the mu, sigma, kappa or delta opioid receptor, or ORL1 receptor. In another embodiment, the opioid compound is capable of binding to either: (1) only one of the above-described receptors or (2) all but one the above-described receptors.

Examples of opioid compounds that can be used in the present invention include, but are not limited to: alfentanil, allylprodine, alphaprodine, anileridine, benzylmorphine, beta-hydroxy 3-methylfentanyl, bezitramide, buprenorphine, butorphanol, carfentanil, clonitazene, codeine, cyclazocine, desomorphine, dextromoramide, dezocine, diacetylmorphine (heroin), diampromide, dihydrocodeine, dihydroetorphine, dihydromorphine, dimenoxadol, dimepheptanol, dimethylthiambutene, dioxaphetylbutyrate, dipipanone, eptazocine, ethoheptazine, ethylmethylthiambutene, ethylmorphine, etonitazene, etorphine, fentanyl, hydrocodone, hydromorphone, hydroxypethidine, isomethadone, ketobemidone, LAAM, levallorphan, levorphanol, llevophenacylmorphan, lofentanil, meperidine, meptazinol, metazocine, methadone, O-methylnaltrexone, metopon, morphine, myrophine, nalbuphine, nalorphine, naloxone, naltrexone, narceine, nicomorphine, norlevorphanol, normethadone, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene, remifentanil, sufentanil, tildine, tramadol, salts thereof, mixtures of any of the foregoing, mu-agonists, mixed mu-agonists and antagonists, mu-antagonists, combinations of the preceding and the like, or any pharmaceutically acceptable salt(s) thereof, immediate or sustained release formulations.

In one embodiment, the opioid compound is a naturally occurring opium alkaloid, preferably morphine, codeine, thebaine, papaverine, or noscapine. In another embodiment, the opioid compound is a semi-synthetic opium alkaloid, preferably heroin, hydromorphone, metapon, oxymorphone, levorphanol, hydrocodone, oxycodone, tramadol, nalorphine, naloxone, or naltrexone. In another embodiment, the opioid compound is a synthetic opium alkaloid, preferably meperidine and congners, methadone and congeners, levorphanol and congeners, phenazocine, fentanyl, propoxyphene, or ethoheptazine.

The opioid compound can be a phenathrene, phenylheptylamine or phenylpiperidine. Examples of phenathrenes include, but are not limited to, morphine (MS Contin), heroin, hydromorphone (Dilaudid), oxymorphone (Numorphan), codeine (Tylenol 3, 4), hydrocodone (Vicodin, Lorcet), oxycodone, and etorpine (Immobilon). Commercially available oxycodone formulation include: OxyContin, Supeudol, Roxycodone, Endocet, Oxycet, Percocet, Roxicet, Roxilox, Tylox, Percodan, Roxiprin, Oxycodan. Examples of phenylheptylamines include, but are not limited to, methadone, methadyl acetate, dimeheptanol (methadol), isomethadone, dipipanone, dimenoxadol, and propoxyphene (Darvon). Examples of phenylpiperidines include, but are not limited to, meperidine (Demerol), properidine, alphaprodine, beta-promedol, alfentanyl (Alfenta), fentanyl (Sublimaze), carfentanyl, lofentanil, and sufentanil (Sufenta).

Two different opioid compounds can be combined for administration: a first component and a second component. In one embodiment, the first component is an opioid agonist and the second component is an opioid antagonist. Preferably, the second component blocks at least a portion of the action of the first component. This blocking results in a reduction of adverse side-effects, such as one or more of addiction, constipation, and sedation. In a preferred combination, the first component is morphine, tramadol or hydrocodone, and the second component is naltrexone. The first and second components can be administered as a pre-mixed combination, or can be administered separately.

An opioid antagonist can be a partial agonist-antagonist or a narcotic antagonist. Examples of partial agonist-antagonists include, but are not limited to, noscapine, pentazocine (Talwin), butorphanol (Stadol), and nalbuphine (Nubain). Examples of pure narcotic antagonists include, but are not limited to, naloxone, nalorphine (Nalline), naltrexone (ReVia), nalmefene and nadide (Enzopride).

Thebaine and derivatives and analogues thereof can be synthesized by the methods disclosed by U.S. Pat. Nos. 6,136, 817 and 6,365,742. 14-Hydroxydihydro-morphinones, including oxymorphone, naloxone, naltrexone, oxymorphazone, naloxazone, naltrexazone, oxymorphonazine, naloxonazine, and naltrexonazine, and analogues thereof can be synthesized by the methods disclosed by U.S. Pat. No. 4,803, 208. Morphine derivatives and analogues thereof can be synthesized by the methods disclosed by U.S. Pat. Nos. 6,150, 524 and 6,476,044. Opioids and opioid antagonists include the compounds disclosed by U.S. Pat. Nos. 4,816,586 and 5,352,680, and U.S. Patent Application Publication No. US 2001/0047005.

Pharmaceutical Formulations and Modes of Administration

The present invention also encompasses the use of an opioid compound effective to reduce paresis or paralysis in the manufacture of a medicament for use in treating a neurologic or neurogenic disorder in a subject in need of such treatment. The medicament is effective or efficacious in the treatment of any of the neurologic or neurogenic disorder disclosed above. The medicament can further comprise a mixture of two or more opioid compounds. The medicament can be of an immediate or sustained release form. Preferably the medicament is administered solely or only for treating a neurologic or neurogenic disorder, i.e., it is administered to a subject not in need of pain relief (including relief of moderate to severe pain in an acute or chronic setting), anesthesia, emesis or an anticholinergic effect.

The pharmaceutical compositions can be administered by any suitable route including but not limited to oral, rectal, nasal, topical (including but not limited to transdermal, aerosol, buccal, and sub-lingual), parenteral (including but not limited to subcutaneous, intramuscular, intravenous, intraperitoneal, intrathecal, and intracranial), or by inhalation (including but not limited to nebulization, or by propellant atomizer or propellant inhaler).

The preferred route of administration will depend on many variables (age, condition of the patient, concurrent diseases, formulations available for delivery). Depending on the specific mode of administration, the pharmaceutical compositions may be in the form of a solid, semi-solid, or liquid. Examples include but are not limited to tablets, suppositories, powders, liquids, suspensions, creams, ointments, lotions or the like, preferably in unit dosage form for single administration of a precise dosage. The pharmaceutical composition comprises a therapeutically effective amount of the opioid compound. The pharmaceutical composition can further comprise a pharmaceutically or veterinary acceptable carrier. The pharmaceutical composition can further comprise other pharmaceutical agents, adjuvants, diluents, buffers, etc. The carrier must be "acceptable" in the sense of being compatible with the other ingredients of the formulation and not injurious to the patient.

For solid compositions, conventional nontoxic solid carriers include, for example, but are not limited to pharmaceutical grades of mannitol, lactose, starch, magnesium stearate, sodium saccharin, talc, cellulose, glucose, sucrose, magnesium carbonate, and the like. Liquid pharmaceutically administratable compositions can, for example, be prepared by dissolving, dispersing, etc., an active compound as described herein and an optional pharmaceutical adjuvant in an excipient, such as (without limitation) water, saline, aqueous dextrose, glycerol, ethanol and the like, to thereby form a solution or suspension. If desired, the pharmaceutical composition to be administered may also contain minor amounts of nontoxic auxiliary substances such as (without limitation) wetting or emulsifying agents, pH buffering agents and the like, for example, sodium acetate, triethanolamine oleate, etc. Actual methods of preparing such dosage forms are known, or will be apparent, to those skilled in this art; for example, see Remington: The Science and Practice of Pharmacy, Nineteenth Ed. (Easton, Pa.: Mack Publishing Company, 1995).

Formulations of the present invention suitable for oral administration may be presented as discrete units such as, but not limited to capsules, cachets or tablets, each containing a predetermined amount of the active ingredient; as, but not limited to a powder or granules; as a solution or suspension in an aqueous or non-aqueous liquid; or as an oil-in-water liquid emulsion or a water-in-oil emulsion. The active ingredient may also be presented as a bolus, electuary or paste.

A tablet may be made by compression or molding, optionally with one or more accessory ingredients. Compressed tablets may be prepared by compressing in a suitable machine, the active ingredient in a free-flowing form such as, but not limited to a powder or granules, optionally mixed with but not limited to a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

The opioid useful herein may be delivered through the skin using conventional transdermal drug delivery systems, i.e., transdermal "patches" wherein the agent is typically contained within a laminated structure that serves as a drug delivery device to be affixed to the skin. In such a structure, the drug composition is typically contained in a layer, or "reservoir," underlying an upper backing layer. The laminated device may contain a single reservoir, or it may contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or it may take some other form.

Pharmaceutical compositions for topical administration according to the present invention may also be formulated as, but not limited to an ointment, cream, suspension, lotion, powder, solution, paste, gel, spray, aerosol or oil.

Formulations for rectal administration may be presented as a suppository with a suitable base comprising, for example, cocoa butter, or a salicylate.

Formulations suitable for nasal administration, wherein the carrier is a solid, include a coarse powder having a particle size, for example, in the range of about 20 to about 500 microns, which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the agent.

Formulations suitable for parenteral administration include aqueous and non-aqueous isotonic sterile injection solutions that may contain anti-oxidants, buffers, bacteriostats and solutes which render the formulation isotonic with the blood of the intended recipient; suspending agents and thickening agents, and liposome's or other microparticulate systems which are designed to target the compound to blood components or one or more organs. The formulations may be presented in unit-dose or multi-dose sealed containers, for example, ampules and vials, and may be stored in a freeze-dried (lyophilized) condition requiring only the addition of the sterile liquid carrier, for example, water for injection, immediately prior to use. Extemporaneous injection solutions and suspensions may be prepared from sterile powders, granules or tablets of the kind previously described.

The pharmaceutical formulation can deliver the opioid compound prepared in an immediate or sustained-release form. A variety of sustained-release forms of opioids are known in the art (e.g., U.S. Pat. Nos. 5,958,459; 6,103,261; 6,294,195; 6,162,467). To prepare the sustained-release forms, the selected opioids are typically (without limitation) incorporated into a sustained release matrix; incorporated into a sustained-release coating; incorporated as a separated sustained-release layer with an immediate release layer; or are incorporated as a powder, granulation, etc., in a gelatin capsule.

The coatings are typically capable of producing a strong, continuous film that is smooth and elegant, non-toxic, inert and tack-free, capable of supporting other pigments and other coating additives. A variety of hydrophobic substances are suitable for preparing the coating including (without limitation) hydrophobic polymers such as acrylic polymer, methylcellulose, or a mixture thereof.

Preferred sustained-release matrices comprise a polymer including (without limitation) pharmaceutically acceptable gum, an alkylcellulose, a cellulose ether, an acrylic resin, protein-derived materials, and mixtures thereof.

It should be understood that in addition to the ingredients particularly mentioned above, the formulations of this invention can further comprise other agents conventional in the art having regard to the type of formulation in question; for example, those suitable for oral administration may include such further agents as sweeteners, thickeners and flavoring agents. It also is intended that the agents, compositions and methods of this invention be combined with other suitable compositions and therapies.

Dosage

The amount of active agent administered and the dosing regimen used, is dependent on the particular drug selected, the age and general condition of the subject being treated, the severity of the subject's condition, and the judgment of the prescribing physician. Preferably, the daily drug dosage will be administered one to eight times, preferably one to four times daily or over a 48-hour period. Preferably, a daily dose of an active agent when administered ranges from 0.1 mg to 200 mg, depending on the half-life of the drug in the treated subject, the availability of the active compound via the chosen route of administration, and the ability of the drug to sustain a therapeutic level in the patient. The dosing regimen can be modulated in order to achieve the desired effect. In increasing order of preference, a daily dose can range from 0.1 mg to 100 mg, from 0.1 mg to 80 mg, from 1 mg to 80 mg, and from 3 mg to 40 mg. Preferably, when an animal subject is in the range of 60 to 80 pounds, a starting dose of OxyContin®, is 5-10 mg given every 12 hours; if the subject starts to show the symptoms of drug tolerance, the dose is elevated by 5 mg every 12 hours. A starting dose of morphine sulfate extended release for such a subject is 7.5 to 15 mg given every 12 hours; if the subject starts to show the symptoms of drug tolerance, the dose is elevated by 7.5 mg every 12 hours.

The lowest effective dosage is the least amount of the pharmaceutical formulation sufficient to effect treatment of a neurologic or neurogenic disorder or syndrome. The lowest effective dose of an opioid formulation used to control the presenting symptoms in the studies underlying the present invention was, oxycodone immediate release, in suspension, 3 mg administered every 12 hours, to a 47 lb subject.

The highest tolerated dosage is the maximum amount of the pharmaceutical formulation to effect treatment without the occurrence of adverse side effect(s) outweighing the benefit received. The highest tolerated dose of an opioid formulation used in the studies underlying the present invention was OxyContin®, 120 mg. More preferably, this is administered as 2 (40 mg) tabs given every a.m., and 1 (40 mg) tab given every p.m.

The dose of medication is adjusted according to the weight and need of a subject, to ameliorate the presenting symptoms. One of ordinary skill in the art has the means to determine the adjustment needed.

Evaluating Opioid Dosage and Effectiveness

The present invention further encompasses a method for testing or identifying an opioid compound or a pharmaceutical formulation effective for treating a neurologic or neurogenic disorder or syndrome, including the steps: (a) evaluating the function of an organ of a subject, wherein said subject suffers from a neurologic or neurogenic disorder or syndrome, (b) administering an opioid compound or pharmaceutical formulation to said subject, (c) evaluating the function of said organ of said subject, and (d) determining whether said opioid compound or pharmaceutical formulation provided effective treatment. In one embodiment, the method involves repeating steps (a)-(d) for testing or identifying more than one opioid compound or pharmaceutical formulation. When necessary, the method can further involve repeating steps (b) and (c) one or more times for each opioid compound or pharmaceutical formulation tested. Preferably, the function evaluated is lingual, pharyngeal, laryngeal, esophageal, urinary bladder sphincter, lumbar and lumbo-sacral spine, or pelvis and pelvic limb control or function. Preferably, the step of evaluating the function of an organ involves grading the function using a grading system. The compound tested can be either presently known or unknown to be an opioid compound.

In order to evaluate the effectiveness of a dose of an opioid formulation, over time, when being used to treat the symptoms of a neurologic/neurogenic disorder or syndrome, the following grading protocol is a means to quantify and document the neurologic/neurogenic function of the target organ or organs affected by the neuropathy or polyneuropathy at the start and conclusion of a time interval.

In this regard, an organ is considered to be neurologically normal when there is no neuropathology affecting its function. Any partial loss of function in that organ that is neurologic/neurogenic in origin is termed paresis. Total loss of function in that organ that is neurologic/neurogenic in origin is termed paralysis. Because in most cases an organ can be clearly identified as having normal neurologic function, decreased neurologic function (paresis), or no neurologic function (paralysis), the documenting of the degree of remaining neurologic function of an organ lends itself to a simple grading system. An organ that functions normally and is considered to be neurologically normal receives the highest grade of (4). An organ that has no function as a result of a neurologic/neurogenic disorder or syndrome and is paralyzed, receives the lowest grade of (0). An organ that has lost partial function (paresis) as a result of a neurologic/neurogenic disorder or syndrome receives a grade of (1), (2) or (3) depending on the degree of neurologic function remaining.

An increase of the grading of a function in a subject, after administration of an opioid formulation, indicates that the formulation is effective in treating a symptom of the neurologic or neurogenic disorder affecting the function. A greater increase in the grade of neurologic or neurogenic function received while on a medication corresponds to greater effectiveness in providing treatment.

Application of this grading system to the individual disorders described previously proceeds as follows:

Lingual (Paresis/Paralysis): Grade (4)=observation of normal lingual musculature, normal lingual movement while swallowing and normal lingual withdrawal in response to pinching with a hemostat. Grade (0)=atrophy of lingual musculature, inability to swallow a bolus of food, audible choking and gagging and no lingual withdrawal in response to pinching with a hemostat. Grade (1), (2) or (3)=depending on the degree of lingual musculature remaining, the amount lingual movement during attempted swallowing and degree of withdrawal remaining in response to pinching with a hemostat.

Pharyngeal (Paresis/Paralysis): Grade (4)=normal swallowing of a bolus of food or liquid. No audible obstructive airway sounds. No choking, or gagging sounds audible.

Grade (0)=no ability to swallow a bolus of food of liquid, audible obstructive airway sounds with choking and gagging audible. Grade (1), (2) or (3)=depending on the degree of swallow reflex remaining the amount of audible obstructive airway sounds present and the degree of choking and gagging present.

Laryngeal (Paresis/Paralysis): Grade (4)=normal unobstructed flow of air into and out of the larynx with normal vocalization. Grade (0)=obstructed flow of air into the larynx with obstructed upper airway sounds, choking and gagging noted, and loss of vocalization. Grade (1), (2) or (3)=depending on the amount of unobstructed airflow remaining, the amount of choking and gagging noted and the degree of vocalization remaining. An exemplar of a grading system for laryngeal function, further divided into breathing, swallowing, laryngospasm, jaw tone, and overall exposure of the larynx for examination, is described in Gross et al. (*J. Am. Animal Hosp. Assoc.* 38:503-6 2002).

Esophageal (Paresis/Paralysis): Grade (4)=normal passage of a bolus of food or fluid, after swallowing, from the back of the throat into the stomach. Grade (0)=delayed or impaired passage of a bolus of food or fluid, after swallowing, from the back of the throat into the stomach, due to a lack of peristaltic contractions within the esophagus, with possible secondary symptoms of regurgitation, esophageal pain and halitosis. Grade (1), (2) or (3)=depending on the degree of peristaltic muscular contraction remaining in the esophagus and the extent of the impairment to the passage of a bolus of food or fluid from the back of the throat, after swallowing, into the stomach, and the secondary symptoms associated with the impairment.

Urinary Bladder Sphincter (Paresis/Paralysis): Grade (4)=normal urinary bladder sphincter function, normal ability to store and pass urine. Grade (0)=no urinary bladder sphincter function with continual leaking of urine out of the bladder and subsequently out of the urethra, with secondary consequences including urine scald, moist dermatitis, urethritis, cystitis, nephritis. Grade (1), (2) or (3)=depending on the degree of urinary bladder sphincter function remaining and the amount of urine leaking with its secondary side effects.

Lumbar and Lumbo-Sacral Spine (Paresis/Paralysis): Grade (4)=normal amount and function of muscles that are responsible for moving the lumbar and lumbo-sacral spine while bending, moving the back, and supporting the lower torso. Grade (0)=atrophy and loss of all tone of the muscles that are responsible for movement of the lumbar and lumbo-sacral spine rendering the body incapable of supporting the back and lower torso and thus preventing any voluntary movement of this part of the body. Grade (1), (2) or (3)=depending on the amount of muscle and muscle tone remaining and the extent to which voluntary support and movement of the lower back and torso remain.

Pelvis and Pelvic Limb (Paresis/Paralysis): Grade (4)=normal amount and function of muscles that are responsible for extending and flexing the joints of the pelvis and pelvic limbs. Grade (0)=atrophy and loss of all tone of the muscles that are responsible for extending and flexing the joints of the pelvis and pelvic limbs, rendering them incapable of supporting the body and unable to ambulate. Grade (1), (2) or (3)=depending on the amount of muscle and muscle tone remaining and the extent to which voluntary support and movement of the pelvis and pelvic limbs is possible.

The use of opioid formulations for the treatment of specified neurologic/neurogenic disorders are illustrated in the example section below. These examples support the following:

(1) Pharmaceutical formulations from the group of drugs known as "opioids" are effective as a treatment for the neurologic/neurogenic symptoms associated with the disorders including lingual, pharyngeal, laryngeal, esophageal, urinary bladder sphincter, lumbar and lumbo-sacral spine, and pelvis and pelvic limb paresis/paralysis.

(2) When a subject's neurologic/neurogenic symptoms have been ameliorated by the use of a specific pharmaceutical formulation of opioid, substitution of a different, but equivalent pharmaceutical formulation of opioid does not guarantee continued successful treatment of the same symptoms (as in Example 3, where resuming administration of the initial agent successfully re-established treatment). In other subjects (as in Examples 6 and 7) continued successful treatment has been demonstrated after substitutions between sustained and immediate release formulations and between naturally occurring and semi-synthetic opioids.

(3) Different subjects with similar presenting neurologic/neurogenic disorders do not respond the same when treated with the same pharmaceutical formulations of opioids, in the same manner (as in Examples 1 and 2). As further illustrated in Example 2, successful treatment can be accomplished by consideration of the particular subject and symptoms, and adjusting the active agent, the dose and/or the formulation employed.

The examples are provided as a guide to a practitioner of ordinary skill in the art, and are not meant to be limiting in any way.

EXAMPLES

Example 1

The following case study establishes the efficacy of a sustained release formulation of a semi-synthetic opioid agonist, oxycodone hydrochloride (OxyContin®, Purdue Pharma LP, Stamford, Conn.) in particular, in the treatment of pharyngeal paresis/paralysis, laryngeal paresis/paralysis, urinary bladder sphincter paresis/paralysis, lumbar and lumbo-sacral spine paresis/paralysis, and pelvis and pelvic limb paresis/paralysis.

"SR," an 8½ year old spayed, female, Rhodesian Ridgeback (dog), suffered from a neurologic/neurogenic syndrome consisting of the following disorders: pharyngeal paresis/paralysis, laryngeal paresis/paralysis, urinary bladder sphincter paresis/paralysis, lumbar and lumbo-sacral spine paresis/paralysis, and pelvis and pelvic limb paresis/paralysis.

Historically, SR's owner reported a progressive exercise intolerance attributed to an increasing difficulty in breathing and a progressive weakness and incoordination of the rear legs resulting from the loss of muscle mass over the lumbar and lumbo-sacral spine, pelvis and pelvic limbs. Excessive panting, choking and gagging were noted throughout the day even if the temperature is cool and the body is at rest. Leaking of urine was noted as a continual problem and a stagnant urine odor is detectable from the area of the vulva.

On physical examination the mouth was open, and panting with increased airway resistance is audibly noted. The tongue was visibly drier than usual. There was visible muscle atrophy over the lumbar and lumbo-sacral spine, pelvis and pelvic limbs, as evidenced by visible and palpable bony prominences in each of these affected areas. There was a stagnant urine smell coming from the area of the vulva.

The mouth was opened and the tongue extended to allow visualization of the throat. A small but ineffective swallow reflex was noted. The ineffective swallow reflex allowed a small pool of sticky saliva to collect at the opening of the arytenoids, which additionally had lost their paradoxical outward movement during inspiration. The inspiration of pooled, sticky saliva into the tracheal opening caused a continual cough response, which in turn caused chronic inflammation of the arytenoids. Chronic inflammation of the arytenoids caused swelling of the mucosal tissues, increasing resistance to air movement through the swollen and therefore smaller arytenoid opening. More effort was therefore used to inspire.

The initial medication selected to treat the symptoms of this polyneuropathy was the sustained release, semi-synthetic, opioid agonist oxycodone hydrochloride, 20 mg/tablet, dosed at ½ tablet every 12 hours.

After 1 week of administration, no further symptoms of pharyngeal or laryngeal paresis/paralysis were reported by the owner. Panting was no longer observed at inappropriate times and the sounds of restrictive air movement were no longer audible. Additionally, it was reported that the leaking of urine had completely stopped.

After 2 weeks of administration SR's body movement during ambulation, were reported to show an almost complete return to normal. The previously described symptoms of weakness and incoordination were gone. The previously visible bony prominences of the vertebrae, pelvis and pelvic limbs were now almost completely covered with visible and palpable muscle tissue. Further, the owner reported that the urinary incontinence had stopped.

Example 2

The following case study establishes the efficacy of an immediate release formulation of a semi-synthetic opioid agonist, oxycodone hydrochloride (Roxicodone®), for the treatment of lingual paresis/paralysis, pharyngeal paresis/paralysis, laryngeal paresis/paralysis, esophageal paresis/paralysis, urinary bladder sphincter paresis/paralysis, lumbar and lumbo-sacral spine paresis/paralysis, and pelvis and pelvic limb paresis/paralysis. This case also establishes the utility of an immediate (i.e., not sustained) release formulation of oxycodone hydrochloride to maintain an effective level of medication to effectively treat and resolve this dog's polyneuropathy.

"JS," an 11 year old spayed, female, Standard Poodle (dog), presented with a neurologic/neurogenic syndrome consisting of the following disorders: lingual paresis/paralysis, pharyngeal paresis/paralysis, laryngeal paresis/paralysis, esophageal paresis/paralysis, urinary bladder sphincter paresis/paralysis, lumbar and lumbo-sacral spine paresis/paralysis, and pelvis and pelvic limb paresis/paralysis.

Historically, "JS's" symptoms included, general body weakness, difficulty swallowing, difficult, noisy breathing, reflux of gastric acid into her esophagus, regurgitation of gastric acid from the esophagus into her oral and nasal cavities, with accompanying oral and nasal discharges. Visible wasting of the muscles over her lumbar and lumbo-sacral spine, and pelvis and pelvic limbs made it difficult to rise from a sitting position or walk without stumbling. She also exhibited an uncontrolled leaking of urine.

Her condition was so unstable at presentation that it took 72 hours to sort out and address all of her secondary medical problems. At this point only the above-described underlying, polyneuropathic syndrome remained. The initial medication selected to treat her polyneuropathy was the sustained-release, semi-synthetic opioid agonist, oxycodone hydrochloride (OxyContin). Within 2-3 hours of administering the initial dose (⅛ of a 10 mg tablet every 12 hours), many of the neuropathic symptoms began to subside.

Initially, she appeared more alert and interested in her surroundings. Shortly thereafter, the volume and strength of her respiration began to improve; as it did, most if not all of the obstructed laryngeal sounds seemed to subside. When asked to go outside for a walk, this dog who previously was too weak to stand, stood up, shook herself as if shaking water from her coat, and walked briskly towards the clinic's front door. When outside, she squatted, supporting her weight easily, urinated, stood back up and trotted back to the clinic door. She was sent home with the same medication, dose and dosing interval and her owners instructed to call daily with progress reports.

The following day, JS's owners reported that her condition had deteriorated almost as quickly, overnight, as it had improved the day before. On examination she was in fact very tired and reluctant to move or obey even simple commands such as heal or stand. Her head was hanging and her newly found interest in life had all but receded. Her heart rate, which had been between 120-140 bpm only yesterday, was now only 60-80 bpm at rest. Her respiratory rate, which had been markedly elevated, the prior day, was now very depressed. While these findings were disheartening, one significant difference did remain from SR's condition upon initial presentation. Although her body, heart and respiratory rates were depressed, she was still breathing without any of the obstructive sounds symptomatic of her presenting pharyngeal or laryngeal neuromyopathy.

Medication was discontinued and the owners kept SR stable and reported her vital signs daily. After 48 hours her cardiac and respiratory rates began to rise and other symptoms began to resolve. The symptoms that initially appeared to indicate a relapse turned out to be those of drug-induced depression and were in fact symptoms of an opioid overdose.

After several attempts to adjust SR's medication, it was finally determined that an immediate release formulation of oxycodone hydrochloride (Roxycodone®) effectively controlled the symptoms of her polyneuropathic syndrome. The effective dose and frequency of medication was established to be (2 drops of Roxycodone in syrup, 20 mg/ml, every 12 hours). With this formulation she no longer suffers from the symptoms of general body weakness, lingual, pharyngeal, laryngeal, esophageal, urinary bladder sphincter, lumbar and lumbo-sacral, pelvis and pelvic limb paresis/paralysis.

Example 3

The following case study establishes the effectiveness of a sustained release formulation of a semi-synthetic opioid agonist, oxycodone hydrochloride (OxyContin®) for the treatment of a polyneuropathic syndrome, and the return of the ameliorated symptoms when a sustained release formulation of a naturally occurring opioid agonist, Morphine Sulfate E.R., with an equivalent amount of opioid, was substituted in it's place. The disorders in the syndrome included lingual paresis/paralysis, pharyngeal paresis/paralysis, laryngeal paresis/paralysis, urinary bladder sphincter paresis/paralysis, lumbar and lumbo-sacral spine paresis/paralysis, and pelvis and pelvic limb paresis/paralysis.

"ML," a 13½ year old, spayed, female, large breed canine cross (dog), suffered with a neurologic/neurogenic syndrome consisting of the following disorders: lingual paresis/paralysis, pharyngeal paresis/paralysis, laryngeal paresis/paralysis, urinary bladder sphincter paresis/paralysis, lumbar and lumbo-sacral spine paresis/paralysis, and pelvis and pelvic limb paresis/paralysis.

Historically her symptoms included, continual panting, dryness of the tongue and mouth, difficulty swallowing, choking, gagging and coughing, inspiratory difficulty accompanied by moist obstructive airway sounds, snoring, and progressive rear leg weakness especially noticeable because of the muscle atrophy seen over her lumbar and lumbo-sacral spine, pelvis and pelvic limbs. ML's owners had also noticed a problem with leaking of urine over the previous few years.

The medication selected to treat her polyneuropathy is the sustained release, semisynthetic opioid agonist, oxycodone hydrochloride (OxyContin®), one 10 mg tablet, given orally every 12 hours. Within the first six hours after starting the medication, the lingual, pharyngeal and laryngeal symptoms had all but abated. After the first week on medication all the symptoms of her urinary tract incontinence began to recede. By the 3rd week after starting the medication, most of the muscle mass had returned to the lumbar and lumbo-sacral spine, pelvis and pelvic limbs. For the next several months she stayed on the same dose and frequency of (OxyContin®), 10 mg administered every 12 hours. This provided a stable therapeutic blood level, which ameliorated all the symptoms of the aforementioned polyneuropathic syndrome.

Because of cost issues, the owner elected to change the medication to an equivalent amount of the sustained release opioid agonist, Morphine Sulfate E.R., one 15 mg/tab, given every 12 hours. After one week on the new medication, all of the previous symptoms of her polyneuropathic syndrome had returned. She was again choking, gagging and coughing, having trouble swallowing, and showing symptoms of respiratory distress, especially when stressed or when exercising and urine staining was noted in areas where she had been resting or sleeping. The most surprising finding, however, was an almost complete loss of muscle mass over her lumbar and lumbo-sacral spine, and down her pelvis and pelvic limbs, which accompanied the return of weakness and incoordination in these areas.

The owner was instructed to discontinue the Morphine Sulfate E.R. and to immediately resume administration of the previously prescribed dose of OxyContin®; 24 hours after resumption, the owner reported complete return of the laryngeal, pharyngeal, and lingual function. Over the next two weeks the function and muscling of the lumbar and lumbo-sacral spine, pelvis and pelvic limbs returned, as did the patency of the urinary bladder sphincter.

Example 4

"KP," a three year old, neutered, male, Siberian Husky (dog), was medicated with high dose (OxyContin® 40 mg am, and 60 mg pm) for the treatment of an inherited form of laryngeal paresis/paralysis. The treatment has been effective in ameliorating the laryngeal paresis/paralysis.

Example 5

"PJ," a seventeen year old, neutered, male, Belgium Shepard (dog), was treated with (OxyContin® 10 mg every 12 hours) for the treatment of lingual, pharyngeal, laryngeal, urinary bladder sphincter, lumbar and lumbo-sacral, pelvis and pelvic limb paresis/paralysis. The treatment has been effective in eliminating or reducing these neuromyopathic symptoms.

Example 6

"MG," a thirteen year old, neutered, male, mid-sized, Terrier cross (dog), was initially treated with Morphine Sulfate E. R. (15 mg, ½ tab every 12 hours), which was replaced by OxyContin® (10 mg every 12 hours) to treat the symptoms associated with a polyneuropathy which included: lingual, pharyngeal, laryngeal, and pelvis and pelvic limb paresis/paralysis. The replacement with OxyContin® has also effectively reduced the neuromyopathic symptoms.

Example 7

"LG," a fourteen year old, spayed, female, Golden Retriever (dog), was initially treated with Morphine Sulfate, Immediate Release, Suspension (20 mg/ml, 5-10 drops every 12 hours), which was replaced with oxycodone Extended Release (15 mg, ½ tab every 12 hours) to treat the symptoms associated with a polyneuropathy which included: lingual, pharyngeal, laryngeal, and pelvis and pelvic limb paresis/paralysis. The replacement treatment has also been effective in reducing the neuromyopathic symptoms.

Although the invention has been described with reference to the presently preferred embodiments, it should be understood that various modifications can be made without departing from the spirit of the invention. All publications, patents, patent applications, and web sites are herein incorporated by reference in their entirety to the same extent as if each individual publication, patent or patent application was specifically and individually indicated to be incorporated by reference in its entirety. The disclosure of each individual publication, patent or patent application is not an admission that each is a prior art reference.

What is claimed is:

1. A method for treating paresis/paralysis resulting from a neurologic or neurogenic disorder comprising administering to a subject in need thereof an effective amount of an opioid compound, wherein said neurologic or neurogenic disorder is: lingual, pharyngeal, laryngeal, or esophageal paresis/paralysis.

2. The method of claim 1, wherein said subject suffers from a syndrome comprising more than one of the disorders: lingual, pharyngeal, laryngeal and esophageal paresis/paralysis.

3. The method of claim 1, wherein said opioid compound is a naturally occurring opium alkaloid.

4. The method of claim 3, wherein said naturally occurring opium alkaloid is morphine, codeine, thebaine, papaverine, or noscapine, or a pharmaceutically or veterinarily acceptable salt thereof.

5. The method of claim 1, wherein said opioid compound is a semi-synthetic opium alkaloid.

6. The method of claim 5, wherein said semi-synthetic opium alkaloid is hydromorphone, metapon, oxymorphone, levorphanol, hydrocodone, oxycodone, tramadol, nalorphine, naloxone, or naltrexone, or a pharmaceutically or veterinarily acceptable salt thereof.

7. The method of claim 1, wherein said opioid compound is a synthetic opium alkaloid.

8. The method of claim 7 wherein said synthetic opium alkaloid is meperidine, methadone, levorphanol, phenazocine, fentanyl, propoxyphene, or ethoheptazine, or a pharmaceutically or veterinarily acceptable salt thereof.

9. The method of claim 1, wherein said opioid compound is in an immediate or sustained release pharmaceutical formulation.

10. The method of claim 9, wherein said pharmaceutical formulation is a sustained release formulation.

11. The method of claim 1, wherein said pharmaceutical formulation is administered about no more than eight times within a twenty-four hour period.

12. The method of claim 1, wherein said compound is administered to the subject in a daily dose range of about 0.1 mg to 200 mg.

13. The method of claim 12, wherein said compound is administered to the subject in a daily dose range of about 1 mg to 100 mg.

14. The method of claim 1, wherein said compound is administered orally, intravenously, intramuscularly, subcutaneously, or transdermally.

15. The method of claim 1, wherein the subject is a mammal.

16. The method of claim 1, comprising administering two different opioid compounds wherein the first opioid compound is an opioid agonist and the second opioid compound is an opioid antagonist.

17. The method of claim 16 where said opioid agonist is morphine, oxycodone, tramadol or hydrocodone or a pharmaceutically or veterinarily acceptable salt thereof.

18. The method of claim 16 where said opioid antagonist is naltrexone.

19. The method of claim 17 where said opioid antagonist is naltrexone.

20. The method of claim 1 where said compound is oxycodone or morphine or a pharmaceutically or veterinarily acceptable salt thereof.

21. The method of claim 1 where said compound is oxycodone or a pharmaceutically or veterinarily acceptable salt thereof.

22. The method of claim 1 where said compound is sustained release oxycodone or a pharmaceutically or veterinarily acceptable salt thereof.

23. The method of claim 1 where said subject suffers from a syndrome that is neuropathic or polyneuropathic in origin.

24. The method of claim 1 where said treatment at least partially reverses paresis/paralysis associated with said disorder.

25. The method of claim 15 wherein the mammal is a dog.

* * * * *